(12) United States Patent
Cady

(10) Patent No.: US 6,193,677 B1
(45) Date of Patent: Feb. 27, 2001

(54) SONIC PERCUSSOR DEVICE

(75) Inventor: Alan D. Cady, Great Falls, MT (US)

(73) Assignee: B.R.S. Capital, Inc., Scottsdale, AZ (US)

( * ) Notice: Subject to any disclaimer, the term of this patent is extended or adjusted under 35 U.S.C. 154(b) by 0 days.

(21) Appl. No.: 09/131,850

(22) Filed: Aug. 10, 1998

Related U.S. Application Data

(60) Provisional application No. 60/069,320, filed on Aug. 14, 1997.

(51) Int. Cl.[7] .................................................. A61M 1/00
(52) U.S. Cl. .................................................. 601/1; 601/47
(58) Field of Search ............................... 601/1, 4, 46, 67, 601/68, 107, 108, 111, 15, 18, 21, 41; 606/201, 203

(56) References Cited

U.S. PATENT DOCUMENTS

| | | | |
|---|---|---|---|
| Re. 32,785 | * 11/1988 | Hirano | ........................ 381/194 |
| 4,079,733 | 3/1978 | Denton et al. . | |
| 4,508,107 | 4/1985 | Strom et al. . | |
| 4,512,339 | 4/1985 | McShirley . | |
| 4,697,581 | 10/1987 | Endo et al. . | |
| 4,710,655 | 12/1987 | Masaki . | |
| 4,745,910 | 5/1988 | Day et al. . | |
| 4,791,915 | 12/1988 | Barsotti et al. . | |
| 4,838,263 | 6/1989 | Warwick . | |
| 4,977,889 | 12/1990 | Budd . | |
| 5,035,235 | 7/1991 | Chesky . | |
| 5,101,810 | * 4/1992 | Skille et al. | ........................... 601/47 |
| 5,113,852 | * 5/1992 | Murtonen | ............................... 601/47 |
| 5,156,143 | 10/1992 | Bocquet et al. . | |
| 5,167,226 | 12/1992 | Laroche et al. . | |
| 5,261,394 | * 11/1993 | Mulligan et al. | ................... 601/108 |
| 5,453,081 | * 9/1995 | Hansen | ................................ 601/150 |
| 5,829,429 | * 11/1998 | Hughes | ................................ 601/41 |

FOREIGN PATENT DOCUMENTS

233074 * 2/1986 (DE) .

* cited by examiner

*Primary Examiner*—Justine R. Yu
(74) *Attorney, Agent, or Firm*—Schweitzer Cornman Gross & Bondell LLP

(57) ABSTRACT

An apparatus for assisting in the clearing of secretion from the lungs of a patient utilizes sonic pressure waves applied to the chest by an appropriate sound-generating transducer. A control unit allows the generation of a plurality of electrical signals at separate audio frequencies, which signals are combined and intermixed and amplified for driving the transducer. In general, the frequencies are in the range of 100–300 hz. A first frequency is chosen to coagulate the lung secretions, while the application of subsequent frequency signals breaks the secretions and facilitates their migration from the lungs. The use of sonic pressure waves minimizes trauma to the patient.

5 Claims, 3 Drawing Sheets

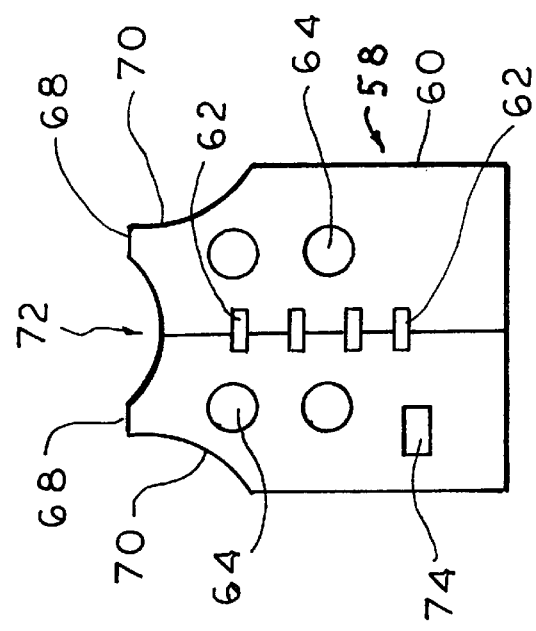
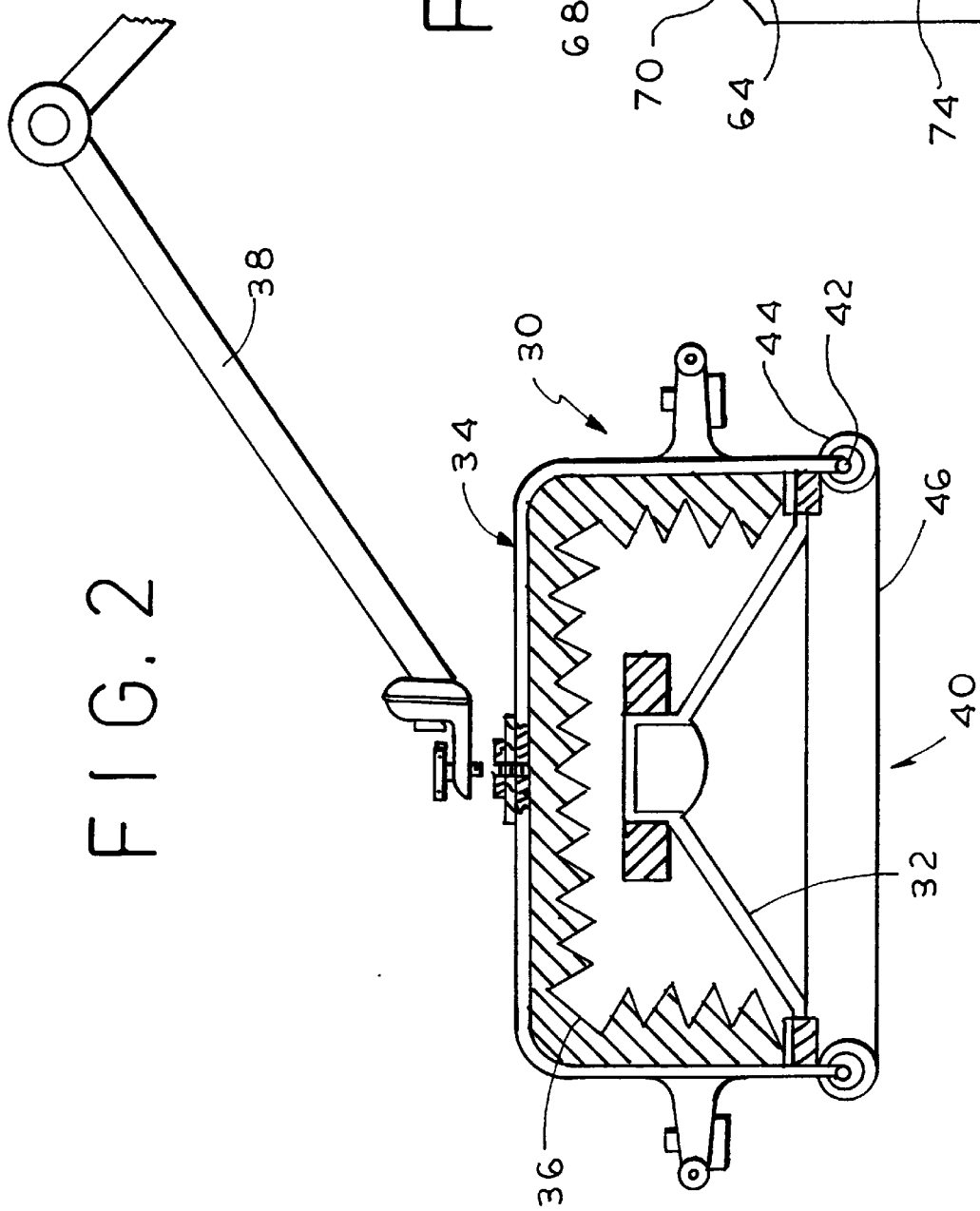

SONIC PERCUSSOR DEVICE

This application claims the priority of Provisional application Ser. No. 60/069,320 filed Aug. 14, 1997.

The present invention relates to a medical device and, in particular, to an audio-driven, oscillatory chest-compression device.

BACKGROUND OF THE INVENTION

The major airways of mammalian respiratory systems are lined with cilia having a protective blanket of mucous. Such a blanket, along with the cough reflex, serve as a primary protective mechanism for the lungs. A variety of pathological conditions result in an increase in the fluids in the lungs: the common cold, infectious diseases; pneumonia; various diseases associated with AIDS; and cystic fibrosis are among the most prevalent. cystic fibrosis, for example, affects the mucous secreting glands of the body, causing an overproduction of mucous. The lungs are continuously filled with such secretions, which must be periodically removed to permit lung function and limit the risk of infection. In addition, the administration of certain anesthetic agents, and soreness and stiffness which may be associated with certain medical procedures, can result in lung secretions tending to pool up and to thicken.

The application of mechanical vibrations or oscillations to the patient to loosen such secretions is known. Typically, a mechanical coupling is made to the patient's body at a location overlying the lung area and a mechanical vibration is applied. One well known therapy is the use of a clapping or thumping upon the chest. The use of the hand, clapped directly against the chest or back with force necessary to release the secretions, can cause unacceptable patient discomfort and trauma. The use of hammer-like products, such as disclosed in U.S. Pat. No. 4,745,910 bring with them similar risks. In addition, as the striking face of the hammer is relatively small, and must be employed with some precision. It is also further necessary to continue the strokes continuously over a wide surface area of the body.

Other mechanical devices, such as disclosed in U.S. Pat. No. 5,167,226, utilize a complex mechanical arrangement of springs and cams to apply a series of vibrations to the patient. Aside from the discomfort that often results from the direct application of the compressive device to the body, such devices are also large and cumbersome.

It is accordingly a purpose of the present invention to provide a percussor-type device which does not require a direct mechanical linkage to the patient.

A further purpose of the present invention is to provide a percussor apparatus capable of generating percussive vibrations at a plurality of frequencies simultaneously or alternatively in accordance with the requirements of the operator and patient.

Still another purpose of the present invention is to provide a percussor apparatus which utilizes sonic energy as the motive force.

BRIEF DESCRIPTION OF THE INVENTION

In accordance with the foregoing and other objects and purposes, a percussor device of the present invention utilizes an electronic system to generate audio frequency signals at frequencies appropriate for stimulating the release of mucous secretions and the subsequent migration of such released secretions for expulsion by the patient. The electronic signals are converted to sonic energy by an appropriate transducer, which may be in the form of a moving coil speaker. The sonic output of the audio transducer or speaker is directed against the body. The sympathetic vibrations generated in the thoracic cavity in response to the application of the sonic compression and rarification are highly effective in releasing and commencing secretion flow. One or multiple transducers can be employed in a variety of configurations to allow the sonic energy to be best directed to the body in consideration of patient needs and limitations. The electronic signals may be interspaced and combined as dictated by the needs of the patient, allowing a variety of sonic energy patterns to be produced.

BRIEF DESCRIPTION OF THE DRAWINGS

A fuller understanding of the present invention will be accomplished upon consideration of the following detailed description of a preferred, but nonetheless illustrative embodiment thereof, when reviewed in connection with the annexed figures, wherein:

FIG. 2 is a sectional elevational view of a transducer of the present invention;

FIG. 4 is a pictorial view of a second embodiment of the invention.

DETAILED DESCRIPTION OF THE INVENTION

Figure 1:
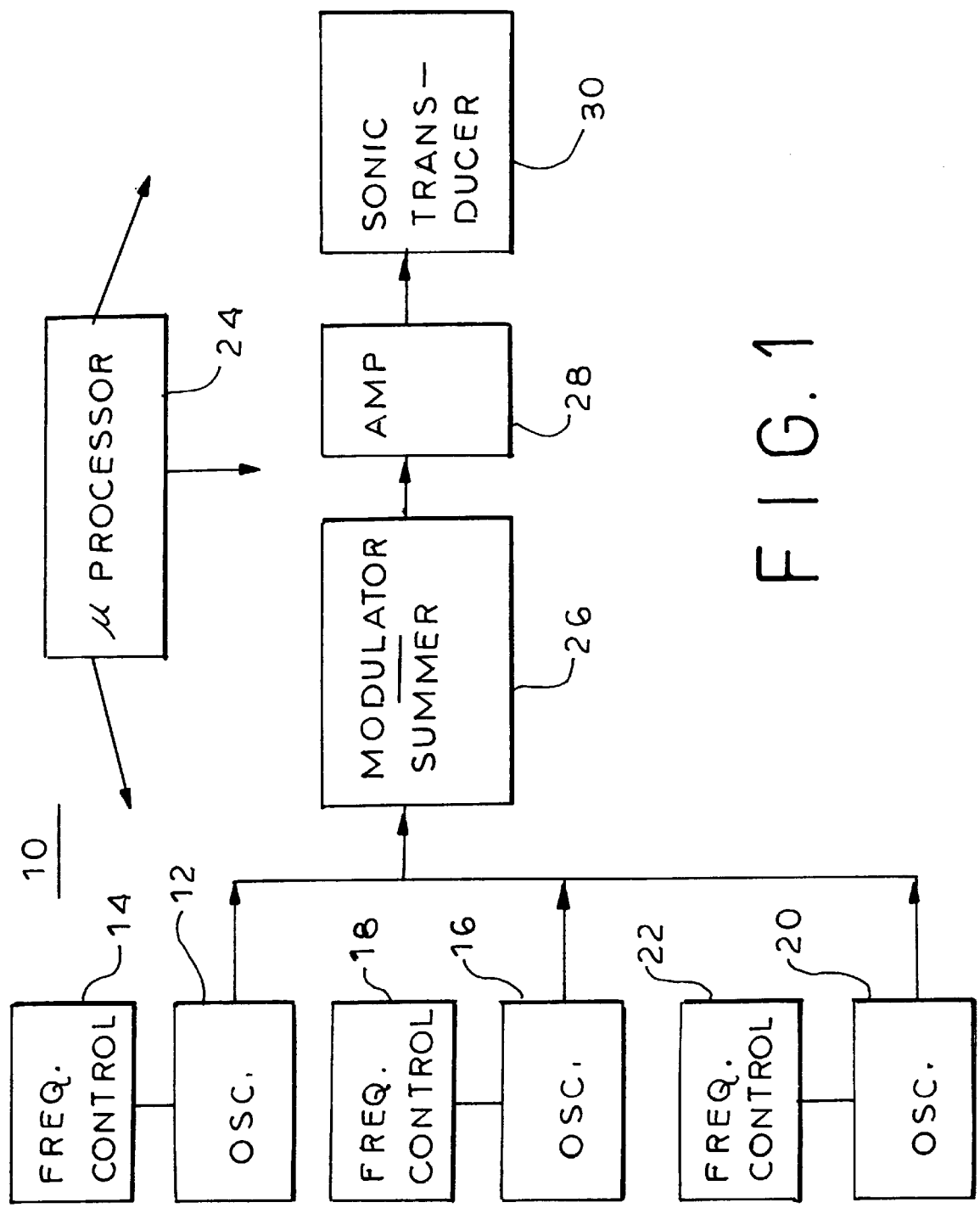
FIG. 1 is a block diagram of the operative components of a percussor device of the present invention.

As depicted in FIG. 1, a sonic percussor apparatus 10 includes first electronic oscillator 12 of a form known in the art capable of generating a sinusoidal output in the audio range. In particular, the oscillator may be capable of generating low frequency outputs in the approximate range of 200 to 300 Hertz. It has been found that such low frequency oscillations are capable of coagulating the mucous secretions into larger masses more capable of subsequent transport out of the pulmonary system. Oscillator 12 is thus preferably provided with frequency control 14 to allow the frequency of the oscillations to be adjusted as desired. Control 14 may preferably include appropriate readouts to allow precise identification of the chosen frequency.

Second oscillator 16 and associated frequency control 18 provide a second sinusoidal output at a frequency range of between about 100 and 300 Hertz.

Third oscillator 20 and its associated frequency control 22 provide a third low frequency sinusoidal output at a frequency range of about 100–250 Hz. Alternatively, other waveforms may be utilized, so long as they have a fundamental frequency in the identified preferred range.

The output waveforms from the three oscillators are combined in modulator/summer 26. As known in the art, modulator 26 may include appropriate attenuators to allow the relative amplitude of the three oscillations to be adjusted as required by the operating practitioner. The three waveforms may be combined in a simple additive manner, or may be alternated or combined separately. Overall system control and supervision may be preferred by microprocessor 24 with memory to permit the entry and storage of complex waveform programs which the applying practitioner may develop.

The output of modulator 26 is applied to audio frequency range amplifier 28. The gain of amplifier 28 is variable, and may be under the control of microprocessor 24. The output of the amplifier drives transducer 30. Transducer 30 may be a moving coil speaker analogous to those used in high-fidelity music systems, the speaker having a power handling capability consistent with the output of amplifier 28. The output of a transducer 30 is directed toward and against the chosen portion of the body.

FIG. 2 presents a representation of the transducer 30. A significant advantage of the present invention is that the transducer need not be placed in "hard" contact with the patient. As shown, speaker 32 is mounted within housing 34, which may be lined with sound-absorbing material 36, such as foam, to absorb sonic energy which is not directed towards the patient. The enclosure may be mounted to positioning arm or boom 38 which may be articulated as known in the art to allow the transducer to be positioned as desired without continuous manual support or assistance.

The speaker 32 is oriented towards open face 40 of the enclosure. The exposed edge side wall edge 42 of the enclosure may be surrounded and covered by a ring of soft cushioning material 44, such as a foam or gel bolster, which both protects the edge and allows the enclosure to be placed in gentle contact with the patient. The cushioning material 44 may further serve as a collimator, to assist both in positioning the transducer over the chosen portion of the body and to provide some measure of collimation and direction for the sonic output. The ring also provides some measure of sound damping to the exterior of the transducer and the sound transfer passageway between the speaker and the patient. A thin membrane 46 may be placed across the open end of the enclosure to protect the transducer. the membrane is chosen to be highly resilient at the sonic frequencies of interest to provide minimal damping or attenuation of the audio signal, and to conform to the patient's body when the transducer head is placed in contact therewith. It may, for example, be 0.020 inch thick silicone rubber. Vent holes (seen in FIG. 3) may be placed in the top of the housing to prevent backpressure buildup in the housing.

With the transducer appropriately positioned proximate the patient, the apparatus is energized and percussion commenced. Because of the precision with which both the frequency and amplitude of the applied sonic signals can be controlled, the practitioner is able to maintain consistency during the course of treatment and over a treatment series. Physical trauma and associated pain are virtually eliminated, as the energy transfer is performed through air coupling between the transducer and patient, rather than through direct solid mechanical linkage. Such sonic impulses can be directed through sensitive areas of the chest wall, minimizing pain and physical trauma.

Figure 3:
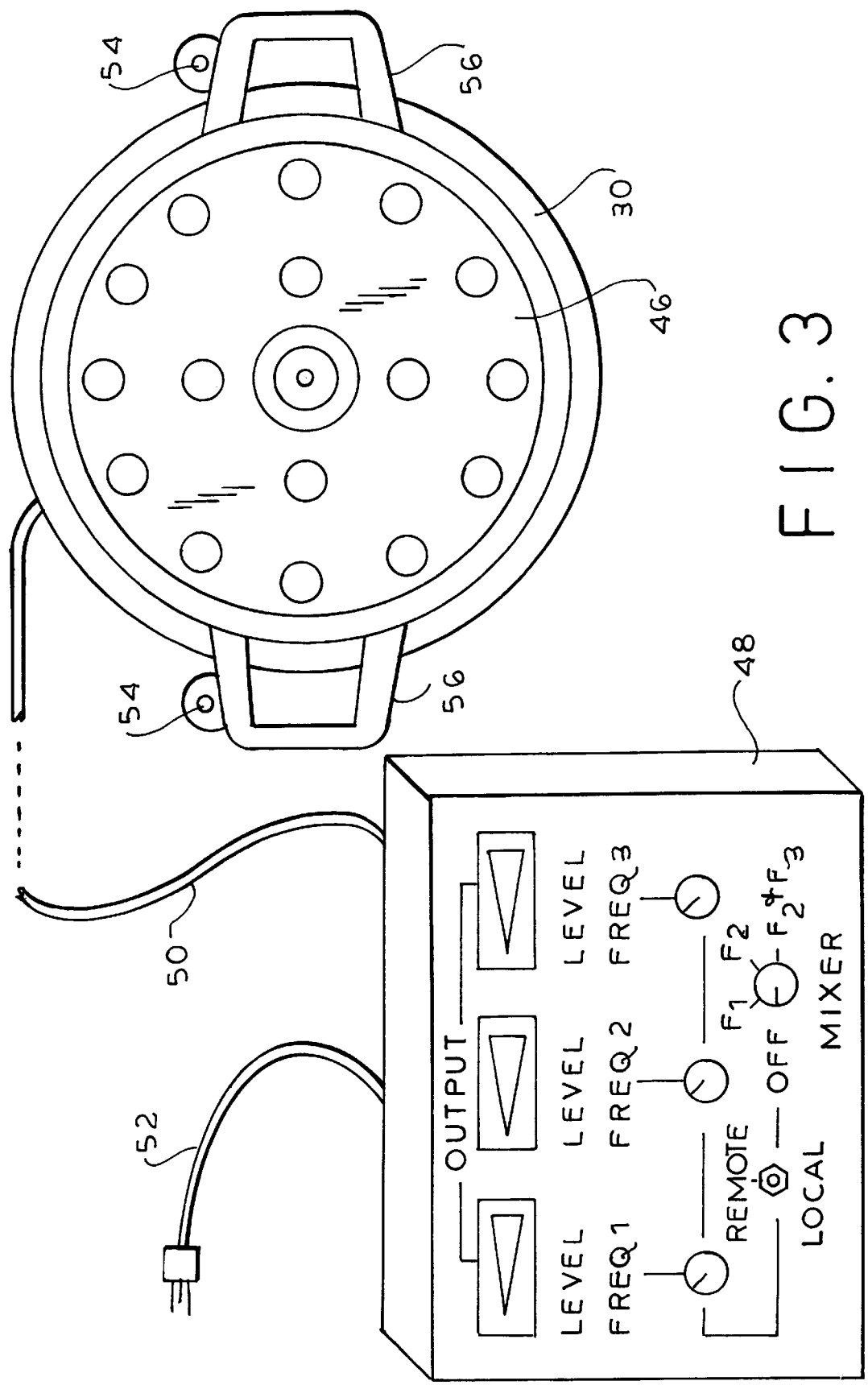
FIG. 3 is a pictorial view of an embodiment of the invention.

As seen in FIG. 3, the transducer 30 is preferably connected to a control console 48 housing the operational electronics by a cable 50. The system may be powered by line current through power cord 52, as known in the art, although alternative power means, such as batteries, can be employed when portability is desired. One or more remote operating switches 54 may be provided on the transducer enclosure, such as on a handle 56, to allow operation of the percussor while the operator is at the patient.

In general, pulse therapy applied by the apparatus may include a first pulse provided by first oscillator 12, intended to break loose relatively large portions of secretions from the lungs. Such pulses may be applied as 30-millisecond bursts at a repetition rate of 1–4 bursts per second. A preferred frequency for the oscillator is 220 Hz. The intensity of the driving signal may range up to about 200 watts peak.

The foregoing bursts may be intermixed with, or followed by similar bursts generated by second oscillator 16. These bursts are intended to further break down the secretions into small portions. The frequency of such oscillations may be chosen from 123.47 Hz, 146.83 Hz, 164.81 Hz, 196.00 Hz and 246.94 Hz. The output power for such bursts is typically about 100 db below that of first oscillator 12.

The output of third oscillator 16 is preferably combined with that of second oscillator 14 in a third burst group. Preferred frequencies for the oscillator include 116.54 Hz, 155.56 Hz, 185.0 Hz and 223.08 Hz. Combined with the output of the second oscillator, the fundamentals and sum and difference frequencies provide a rich audio spectrum, causing the further breakdown of the secretions and facilitating and instituting their expulsion and migration from the lungs.

FIG. 4 depicts an embodiment of the invention in which a plurality of transducers are incorporated into a vest-like unit which may be worn by the patient. As depicted therein, the vest 58, which may be constructed of an appropriate fabric-like material, includes a chest-overlying portion 60 with a pair of shoulder straps 68, arm cutouts 70, and neck scoop 72. A pair of closure devices, such as complimentary hook-and-loop closures 62 allow the vest to be secured snugly about the torso of the patient. A plurality of transducers 64 are located on the vest, and may be particularly positioned to overlie the upper and lower lobes of the lungs. By the use of appropriate transistorized components, it is possible to provide a miniaturized driver 74 for the transducers in a small package which can be mounted directly on the exterior of the vest. Appropriately powered, typically by an interface with a conventional alternating current source or by batteries, such a vest allows therapy to be applied while the patient assumes any of a variety of desired positions. Appropriate circuitry can be incorporated to vary the timing of the drive signals among the individual transducers, if desired.

I claim:

1. A method for effecting clearing of secretions from the lungs, comprising the application of first and second low frequency pulsed audio signals to a chest cavity through a transducer positioned adjacent an overlying skin surface wherein said pulses are of about 30 millisecond duration at a repetition rate of between about 1 to 4 pulses per second.

2. The method of claim 1, further comprising the application of a third low-freqency pulsed audio signal to the chest cavity in combination with the application of the first and second low-frequency pulsed audio signals.

3. The method of claim 1 or claim 2, wherein said first low frequency audio signal is in the range of about 200 to 300 Hertz and said second low frequency audio signal is in the range of about 100 to 300 Hertz.

4. The method of claim 1, wherein a string of said first low frequency pulses is followed by said second low frequency audio signal in the form of a pulse string.

5. The method of claim 2, wherein a string of pulses at said second low frequency is followed by a combination of said second and third audio signals in the form of a pulse string.

* * * * *